(12) United States Patent
Imaizumi et al.

(10) Patent No.: US 10,863,893 B2
(45) Date of Patent: Dec. 15, 2020

(54) ENDOSCOPE APPARATUS

(71) Applicant: OLYMPUS CORPORATION, Tokyo (JP)

(72) Inventors: Katsuichi Imaizumi, Hachioji (JP); Susumu Hashimoto, Hachioji (JP); Suguru Okaniwa, Hachioji (JP); Tomoya Sato, Tokorozawa (JP); Hidekazu Iwaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 350 days.

(21) Appl. No.: 15/970,017

(22) Filed: May 3, 2018

(65) Prior Publication Data

US 2018/0249900 A1 Sep. 6, 2018

Related U.S. Application Data

(63) Continuation of application No. PCT/JP2016/080307, filed on Oct. 13, 2016.

(30) Foreign Application Priority Data

Nov. 10, 2015 (JP) .................................. 2015-220521

(51) Int. Cl.
*A61B 1/00* (2006.01)
*A61B 1/05* (2006.01)
(Continued)

(52) U.S. Cl.
CPC .............. *A61B 1/05* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS 5,398,685 A * 3/1995 Wilk .................... A61B 5/0002
348/65
2005/0240882 A1* 10/2005 Morita ................... G06K 9/033
715/764

(Continued)

FOREIGN PATENT DOCUMENTS

CN 103565411 A 2/2014
CN 104335580 A 2/2015

(Continued)

OTHER PUBLICATIONS

Extended Supplementary European Search Report dated Apr. 10, 2019 in European Patent Application No. 16 86 3940.9.

(Continued)

*Primary Examiner* — Timothy J Neal
(74) *Attorney, Agent, or Firm* — Scully, Scott, Murphy & Presser, P.C.

(57) ABSTRACT

An endoscope apparatus includes a detecting section to which an observation image of a subject is sequentially inputted, the detecting section being configured to detect a characteristic region in the observation image based on a predetermined feature value concerning the observation image, and an emphasis processing section configured to apply, when the characteristic region is continuously detected in the detecting section, emphasis processing of a position corresponding to the characteristic region to the observation image of the subject inputted after elapse of a first predetermined time period from a time when the characteristic region is detected.

21 Claims, 15 Drawing Sheets

(51) Int. Cl.
  *G02B 23/24* (2006.01)
  *G06T 7/00* (2017.01)
  *H04N 5/232* (2006.01)
  *A61B 1/045* (2006.01)
  *H04N 5/225* (2006.01)

(52) U.S. Cl.
  CPC ...... *A61B 1/00045* (2013.01); *A61B 1/00055* (2013.01); *A61B 1/00163* (2013.01); *A61B 1/045* (2013.01); *G02B 23/24* (2013.01); *G02B 23/2423* (2013.01); *G02B 23/2484* (2013.01); *G06T 7/0012* (2013.01); *H04N 5/23293* (2013.01); *G06T 2207/10068* (2013.01); *G06T 2207/30096* (2013.01); *H04N 2005/2255* (2013.01)

(56) References Cited

U.S. PATENT DOCUMENTS

2012/0274754 A1    11/2012  Tsuruoka
2014/0028824 A1     1/2014  Kubo et al.
2015/0077529 A1*    3/2015  Hatta .................. H04N 13/128
                                                            348/54
2016/0038004 A1     2/2016  Tanaka

FOREIGN PATENT DOCUMENTS

| | | | |
|---|---|---|---|
| EP | 2517614 A1 | 10/2012 | |
| EP | 2 863 634 A1 | 4/2015 | |
| JP | 2011-036371 A | 2/2011 | |
| JP | 201136371 * | 2/2011 | ............... A61B 1/04 |
| JP | 2011-160848 A | 8/2011 | |
| JP | 2011-255006 A | 12/2011 | |
| JP | 2015-112429 A | 6/2015 | |
| WO | WO 2011/096279 A1 | 8/2011 | |
| WO | WO-2013187116 A1 * | 12/2013 | ......... A61B 1/00009 |
| WO | 2014/188740 A1 | 11/2014 | |

OTHER PUBLICATIONS

International Search Report dated Dec. 6, 2016 issued in PCT/JP2016/080307.

* cited by examiner

ENDOSCOPE APPARATUS

CROSS REFERENCE TO RELATED APPLICATION

This application is a continuation application of PCT/JP2016/080307 filed on Oct. 13, 2016 and claims benefit of Japanese Application No. 2015-220521 filed in Japan on Nov. 10, 2015, the entire contents of which are incorporated herein by this reference.

BACKGROUND OF THE INVENTION

Field of the Invention

The present invention relates to an endoscope apparatus.

Description of the Related Art

Conventionally, in an endoscope apparatus, a surgeon determines, for example, presence or absence of a lesioned part viewing an observation image. In order to prevent the surgeon from overlooking the lesioned part when viewing the observation image, for example, as described in Japanese Patent Application Laid-Open Publication No. 2011-255006, an endoscope apparatus has been proposed that adds an alert image to a region of interest detected by image processing and displays an observation image.

SUMMARY OF THE INVENTION

An endoscope apparatus according to an aspect of the present invention includes: a detecting section to which an observation image of a subject is sequentially inputted, the detecting section being configured to detect a characteristic region in the observation image based on a predetermined feature value concerning the observation image; and an emphasis processing section configured to apply, when the characteristic region is continuously detected in the detecting section, emphasis processing of a position corresponding to the characteristic region to the observation image of the subject inputted after elapse of a first predetermined time period from a time when the characteristic region is detected and not to apply the emphasis processing of the position corresponding to the characteristic region to the observation image of the subject inputted until the first predetermined time period elapses from the time when the characteristic region is detected.

DETAILED DESCRIPTION OF THE PREFERRED EMBODIMENT(S)

Embodiments of the present invention are explained below with reference to the drawings.

First Embodiment (Configuration)

Figure 1:
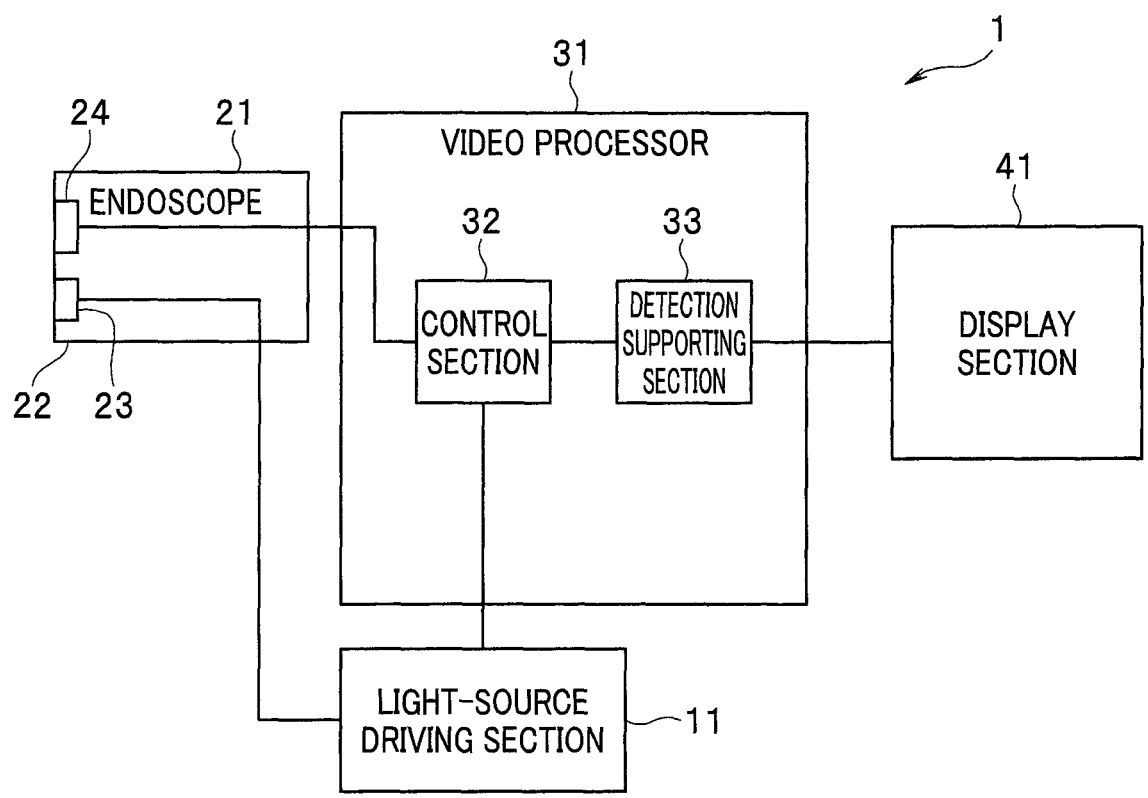
FIG. 1 is a block diagram showing a schematic configuration of an endoscope system according to a first embodiment of the present invention.

FIG. 1 is a block diagram showing a schematic configuration of an endoscope system 1 according to a first embodiment of the present invention.

A schematic configuration of the endoscope system 1, which is an endoscope apparatus, includes a light-source driving section 11, an endoscope 21, a video processor 31, and a display section 41. The light-source driving section 11 is connected to the endoscope 21 and the video processor 31. The endoscope 21 is connected to the video processor 31. The video processor 31 is connected to the display section 41.

The light-source driving section 11 is a circuit that drives an LED 23 provided at a distal end of an insertion section 22 of the endoscope 21. The light-source driving section 11 is connected to a control section 32 of the video processor 31 and the LED 23 of the endoscope 21. A control signal is inputted to the light-source driving section 11 from the control section 32. The light-source driving section 11 is configured to be capable of outputting a driving signal to the LED 23 and driving the LED 23 to cause the LED 23 to emit light.

The endoscope 21 is configured to be capable of inserting the insertion section 22 into a subject and picking up an image in the subject. The endoscope 21 includes an image pickup section including the LED 23 and an image pickup device 24.

The LED 23 is provided in the insertion section 22 of the endoscope 21. The LED 23 is configured to be capable of irradiating illumination light on the subject under control by the light-source driving section 11.

The image pickup device 24 is provided in the insertion section 22 of the endoscope 21. The image pickup device 24 is disposed to be capable of capturing, via a not-shown observation window, reflected light of the subject on which the illumination light is irradiated.

The image pickup device 24 photoelectrically converts the reflected light of the subject captured from the observation window, converts the reflected light from an analog image pickup signal into a digital image pickup signal with a not-shown AD converter, and outputs the digital image pickup signal to the video processor 31.

The video processor 31 is an endoscopic image processing device including an image processing circuit. The video processor 31 includes the control section 32 and a detection supporting section 33.

The control section 32 is capable of transmitting a control signal to the light-source driving section 11 and driving the LED 23.

The control section 32 is capable of applying image adjustment such as gain adjustment, white balance adjustment, gamma correction, contour emphasis correction, and enlargement and reduction adjustment to an image pickup signal inputted from the endoscope 21 and sequentially outputting an observation image G1 of the subject explained below to the detection supporting section 33.

Figure 2:
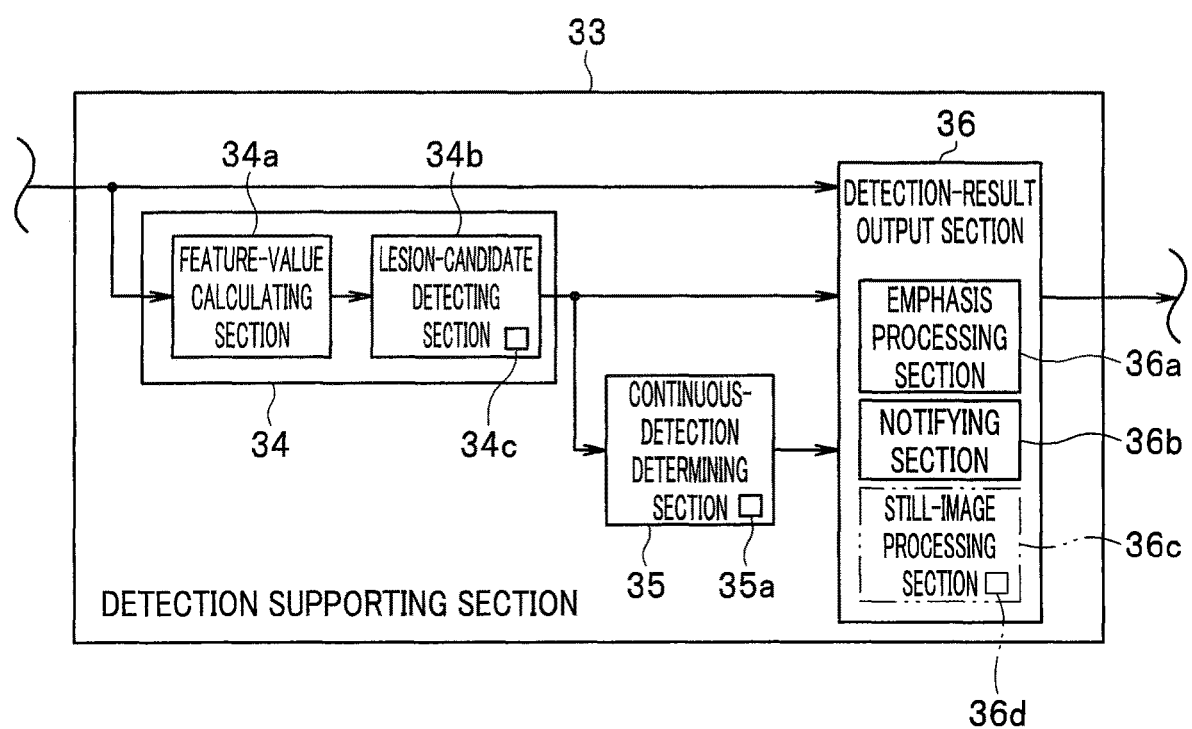
FIG. 2 is a block diagram showing the configuration of a detection supporting section of the endoscope system according to the first embodiment of the present invention.

FIG. 2 is a block diagram showing the configuration of the detection supporting section 33 of the endoscope system 1 according to the first embodiment of the present invention. As shown in FIG. 2, the detection supporting section 33 includes a detecting section 34, a continuous-detection determining section 35, which is a determining section, and a detection-result output section 36.

The detecting section 34 is a circuit to which the observation image G1 of the subject is sequentially inputted, the circuit detecting a lesion candidate region L, which is a characteristic region, in the observation image G1 based on a predetermined feature value concerning the observation image G1. The detecting section 34 includes a feature-value calculating section 34a and a lesion-candidate detecting section 34b.

The feature-value calculating section 34a is a circuit that calculates a predetermined feature value concerning the observation image G1 of the subject. The feature-value calculating section 34a is connected to the control section 32 and the lesion-candidate detecting section 34b. The feature-value calculating section 34a is capable of calculating the predetermined feature value from the observation image G1 of the subject sequentially inputted from the control section 32 and outputting the predetermined feature value to the lesion-candidate detecting section 34b.

The predetermined feature value is calculated by calculating, for each of predetermined small regions on the observation image G1, a change amount, that is, a tilt value between respective pixels in the predetermined small region and pixels adjacent to the pixels. Note that the feature value is not limited to a value obtained by a method of calculating the feature value with the tilt value between the pixels in the predetermined small region and the adjacent pixels. The feature value may be a value obtained by converting the observation image G1 into a numerical value with another method.

The lesion-candidate detecting section 34b is a circuit that detects the lesion candidate region L of the observation image G1 from information concerning the feature value. The lesion-candidate detecting section 34b includes a ROM 34c to be capable of storing a plurality of kinds of polyp model information in advance. The lesion-candidate detecting section 34b is connected to the detection-result output section 36 and the continuous-detection determining section 35.

The polyp model information is configured by feature values of characteristics common to a large number of polyp images.

The lesion-candidate detecting section 34b detects the lesion candidate region L based on the predetermined feature value inputted from the feature-value calculating section 34a and the plurality of kinds of polyp model information and outputs lesion candidate information to the detection-result output section 36 and the continuous-detection determining section 35.

More specifically, the lesion-candidate detecting section 34b compares the predetermined feature value for each of the predetermined small regions inputted from the feature-value detecting section and a feature value of the polyp model information stored in the ROM 34c and detects the lesion candidate region L when the feature values coincide with each other. When the lesion candidate region L is detected, the lesion-candidate detecting section 34b outputs the lesion candidate information including position information and size information of the detected lesion candidate region L to the detection-result output section 36 and the continuous-detection determining section 35.

The continuous-detection determining section 35 is a circuit that determines whether the lesion candidate region L is continuously detected. The continuous-detection determining section 35 includes a RAM 35a to be capable of storing lesion candidate information of an immediately preceding frame. The continuous-detection determining section 35 is connected to the detection-result output section 36.

The continuous-detection determining section 35 determines whether a first lesion candidate region on a first observation image and a second lesion candidate region on a second observation image inputted before the first observation image are the same lesion candidate region L such that the lesion candidate region L can be tracked, for example, even when a position of the lesion candidate region L deviates on the observation image G1. When the same lesion candidate region L is continuously or intermittently detected on a sequentially inputted plurality of observation images G1, the continuous-detection determining section 35 determines that the detection of the lesion candidate region L continues and outputs a determination result to the detection-result output section 36.

The detection-result output section 36 is a circuit that performs output processing of a detection result. The detection-result output section 36 includes an emphasis processing section 36a and a notifying section 36b. The detection-result output section 36 is connected to the display section 41. The detection-result output section 36 is capable of performing emphasis processing and notification processing based on the observation image G1 inputted from the control section 32, the lesion candidate information inputted from the lesion-candidate detecting section 34b, and the determination result inputted from the continuous-detection determining section 35. The detection-result output section 36 outputs an image for display G to the display section 41.

Figure 3:
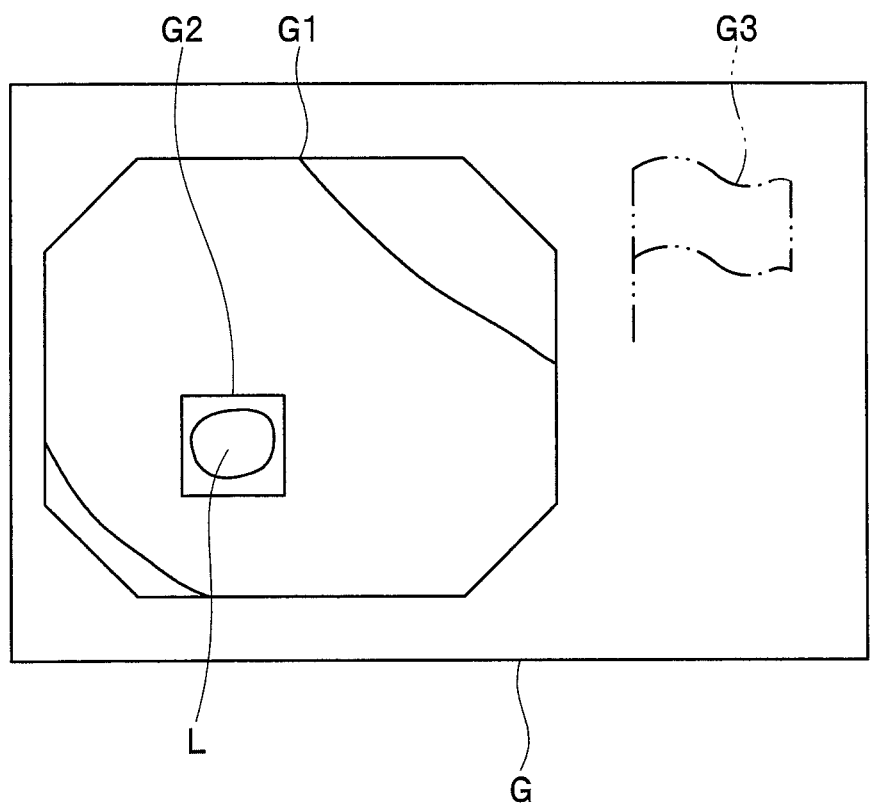
FIG. 3 is an explanatory diagram for explaining an example of a screen configuration of an image for display of the endoscope system according to the first embodiment of the present invention.

FIG. 3 is an explanatory diagram for explaining an example of a screen configuration of the image for display G of the endoscope system 1 according to the first embodiment of the present invention. As shown in FIG. 3, the observation image G1 is disposed in the image for display G outputted from the detection-result output section 36. FIG. 3 shows an inner wall of a large intestine including the lesion candidate region L as an example of the observation image G1.

When the lesion candidate region L is continuously detected in the lesion-candidate detecting section 34b, the emphasis processing section 36a applies emphasis processing of a position corresponding to the lesion candidate region L to the observation image G1 of the subject inputted after elapse of a first predetermined time period from a time when the lesion candidate lesion L is detected.

More specifically, when the lesion candidate region L determined by the continuous-detection determining section 35 as being continuously detected is continuously detected for the first predetermined time period, the emphasis processing is started.

The first predetermined time period is a time period in which a lesioned part can be found from the observation image G1 at high probability by a visual observation of a surgeon. The first predetermined time period is set to, for example, 0.5 second in advance. The first predetermined time period is specified by the number of frames. For example, when the number of frames in one second is thirty, the first predetermined time period is specified by fifteen frames.

The emphasis processing is performed for a maximum of a second predetermined time period. The emphasis processing ends after elapse of the second predetermined time period. When a state in which the lesion candidate region L is continuously detected by the continuous-detection determining section 35 ends before the second predetermined time period elapses, the emphasis processing also ends at that point in time.

More specifically, after the first predetermined time period elapses and the emphasis processing is started, when the second predetermined time period elapses, the emphasis processing ends even if the lesion candidate region L determined by the continuous-detection determining section 35 as being continuously detected is continuously detected.

The second predetermined time period is a time period in which a surgeon can sufficiently recognize the lesion candidate region L from a marker image G2. The second predetermined time period is set to, for example, 1.5 seconds in advance. The second predetermined time period is specified by the number of frames. For example, when the number of frames in one second is thirty, the second predetermined time period is specified by forty-five frames.

The emphasis processing is processing for performing display showing the position of the lesion candidate region L. More specifically, the emphasis processing is processing for adding, based on the position information and the size information included in the lesion candidate information, the marker image G2 surrounding the lesion candidate region L to the observation image G1 inputted from the control section 32. Note that, in FIG. 3, as an example, the marker image G2 is shown as a square. However, the marker image G2 may be any image such as a triangle, a circle, or a star shape. In FIG. 3, as an example, the marker image G2 is a frame image surrounding the lesion candidate region L. However, the marker image G2 may be an image not surrounding the lesion candidate region L as long as the image can show the position of the lesion candidate region L. For example, the position of the lesion candidate region L may be indicated by setting brightness and a color tone of the lesion candidate region L different from brightness and a color tone of a peripheral region.

The notifying section 36b is configured to be capable of notifying, with notification processing different from the emphasis processing, the surgeon that the lesion candidate region L is present in the observation image G1. The notification processing is performed until continuous detection of the lesion candidate region L by the detecting section 34 ends after a time of the elapse of the second predetermined time period when the emphasis processing ends.

The notification processing is processing for displaying a notification image G3 in a region other than the observation image G1. An alternate long and two short dashes line shown in FIG. 3 indicates, as an example, the notification image G3 of a flag pattern. However, the notification image G3 may be any image such as a triangle, a circle, or a star shape.

The display section 41 is configured by a monitor and is capable of displaying, on a screen, the image for display G inputted from the detection-result output section 36.

(Action)

Subsequently, detection result output processing of the detection-result output section 36 is explained.

Figure 4:
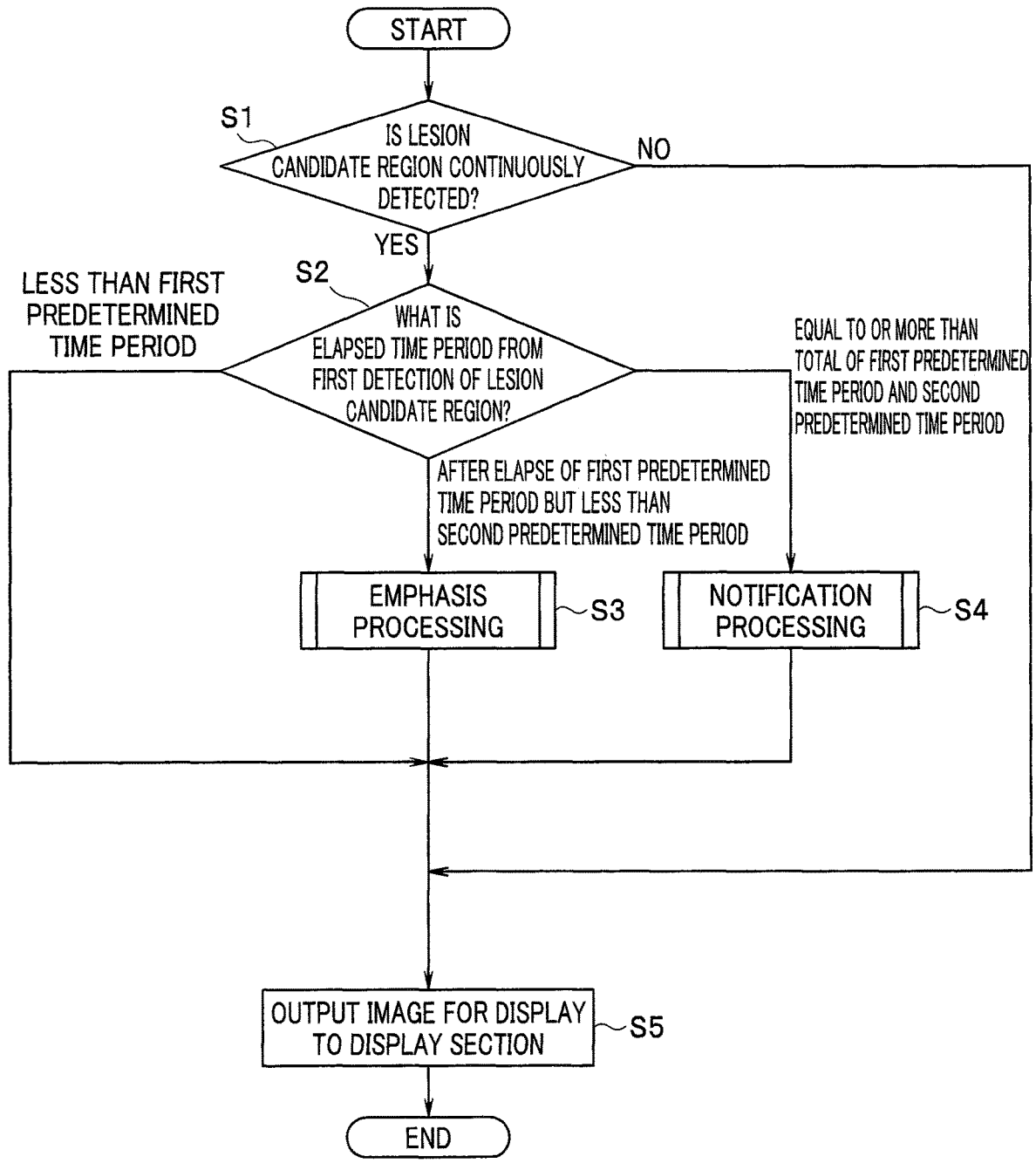
FIG. 4 is a flowchart for explaining a flow of detection result output processing of the endoscope system according to the first embodiment of the present invention.

FIG. 4 is a flowchart for explaining a flow of detection result output processing of the endoscope system 1 according to the first embodiment of the present invention.

When an image of the subject is picked up by the endoscope 21, after image adjustment processing is performed by the control section 32, the observation image G1 is inputted to the detection supporting section 33. When the observation image G1 is inputted to the detection supporting section 33, the feature-value calculating section 34a calculates a predetermined feature value of the observation image G1 and outputs the predetermined feature value to the lesion-candidate detecting section 34b. The lesion-candidate detecting section 34b compares the inputted predetermined feature value and a feature value of the polyp model information and detects the lesion candidate lesion L. A detection result of the lesion candidate region L is outputted to the continuous-detection determining section 35 and the detection-result output section 36. The continuous-detection determining section 35 determines whether the lesion candidate region L is continuously detected and outputs a determination result to the detection-result output section 36.

The detection-result output section 36 determines whether the lesion candidate region L is continuously detected (S1). In S1, the detection-result output section 36 refers to a determination result inputted from the continuous-detection determining section 35. When the detection-result output section 36 determines that the lesion candidate region L is continuously detected (S1: Yes), the processing proceeds to S2. On the other hand, when the detection-result output section 36 determines that the lesion candidate region L is not continuously detected (S1: No), the processing proceeds to S5.

The detection-result output section 36 determines an elapsed time from first detection of the lesion candidate region L (S2). In S2, the detection-result output section 36 determines the elapsed time from the first detection of the lesion candidate region L and, when the detection-result output section 36 determines that the elapsed time is less than the first predetermined time period (e.g., less than 0.5 second, that is, less than 15 frames from the first detection), the processing proceeds to S5. When the detection-result output section 36 determines that the elapsed time is less than the second predetermined time period (e.g., 0.5 second or more to less than 2.0 seconds, that is, 15 frames or more and less than 45 frames from the first detection) after the elapse of the first predetermined time period, the processing proceeds to S3. When the detection-result output section 36 determines that the elapsed time is equal to or more than a total of the first predetermined time period and the second predetermined time period (e.g., 2.0 seconds or more, that is, 45 frames or more from the first detection), the processing proceeds to S4.

In S3, the detection-result output section 36 performs the emphasis processing. In S3, the detection-result output section 36 adds the marker image G2 to the observation image G1. After the processing in S3, the processing proceeds to S5.

In S4, the detection-result output section 36 performs the notification processing. In S4, the detection-result output section 36 performs the notification processing and adds the notification image G3 to the image for display G. After the processing in S4, the processing proceeds to S5.

The detection-result output section 36 outputs the image for display G to the display section 41 (S5).

The processing in S1 to S5 configures the detection result output processing.

Figure 5:
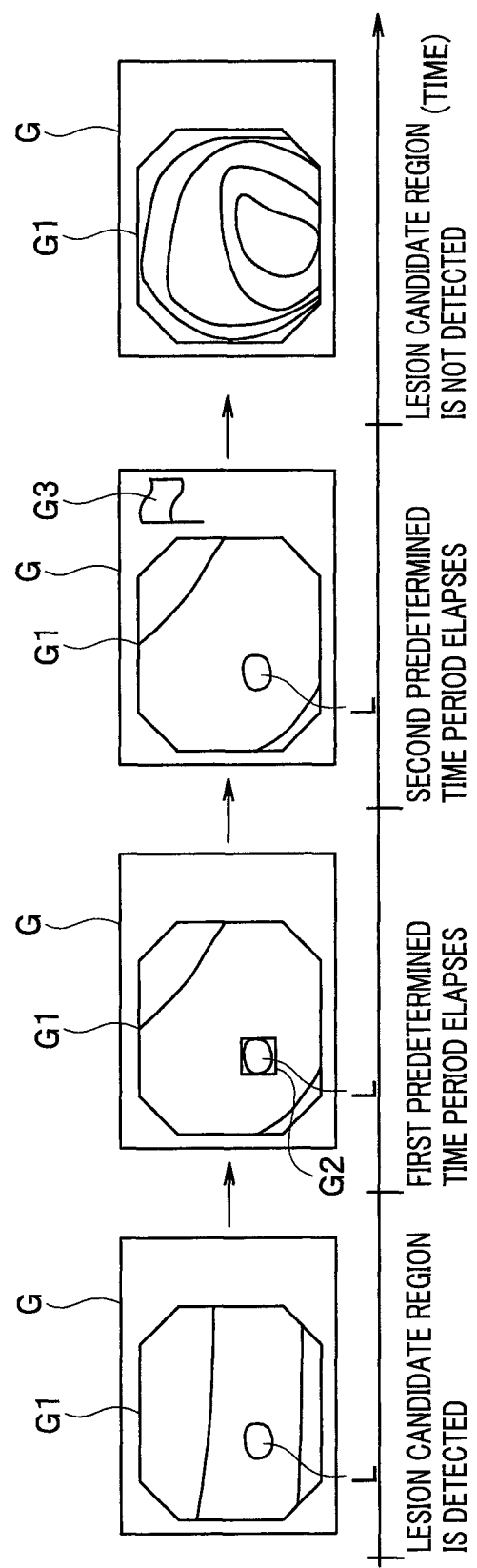
FIG. 5 is an explanatory diagram for explaining an example of screen transition in the detection result output processing of the endoscope system according to the first embodiment of the present invention.

FIG. 5 is an explanatory diagram for explaining an example of screen transition in the detection result output processing of the endoscope system 1 according to the first embodiment of the present invention.

The detection result output processing in S1 to S5 is repeated, whereby the image for display G transitions as shown in FIG. 5.

First, after the lesion candidate region L is detected first, the marker image G2 is not displayed until the first predetermined time period elapses. Subsequently, when the lesion candidate region L is continuously detected for the first predetermined time period, the emphasis processing is started by the emphasis processing section 36a. In the image for display G, the marker image G2 is displayed. Subsequently, when the lesion candidate region L is continuously detected even if the second predetermined time period elapses, the emphasis processing is ended and the notification processing is started by the notifying section 36b. In the image for display G, the marker image G2 is hidden and the notification image G3 is displayed. Subsequently, when the lesion candidate region L is not detected, the notification processing is ended and the notification image G3 is hidden.

According to the first embodiment explained above, there is a time period in which the surgeon visually finds a lesioned part by himself or herself from a time when the lesion candidate region L, which is a region of interest, is detected until the marker image G2 is displayed. It is possible to prevent a decrease in attention to the observation image G1 and present the region of interest to the surgeon without hindering an effort to improve a lesioned part finding ability.

Modification of the First Embodiment

In the first embodiment explained above, the image for display G includes the observation image G1, which is a movie. However, the image for display G may be configured by the observation image G1 and a still image G4.

Figure 6:
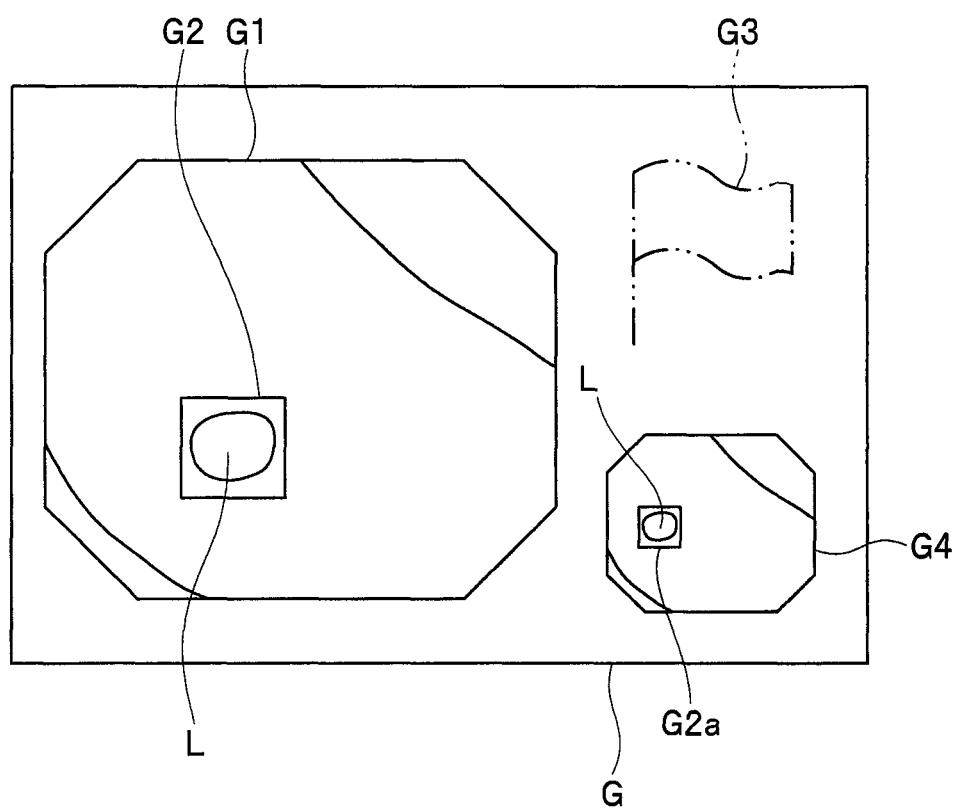
FIG. 6 is an explanatory diagram for explaining an example of a screen configuration of an image for display of an endoscope system according to a modification of the first embodiment of the present invention.
Figure 7:
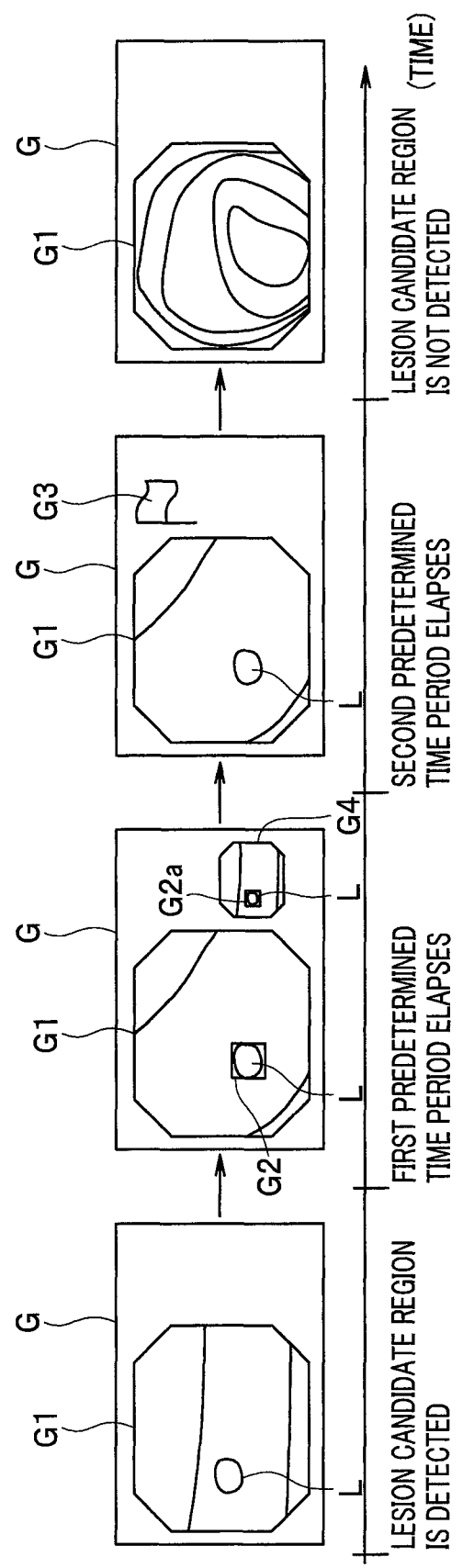
FIG. 7 is an explanatory diagram for explaining an example of screen transition in the detection result output processing of the endoscope system according to the modification of the first embodiment of the present invention.

FIG. 6 is an explanatory diagram for explaining an example of a screen configuration of the image for display G of the endoscope system 1 according to the first embodiment of the present invention. FIG. 7 is an explanatory diagram for explaining an example of screen transition in the detection result output processing of the endoscope system 1 according to a modification of the first embodiment of the present invention.

In the modification of the first embodiment, the detection-result output section 36 includes a still-image processing section 36c and a memory 36d (an alternate long and two short dashes line shown in FIG. 2).

The still-image processing section 36c is configured to be capable of displaying the still image G4 shown in FIG. 6 after the elapse of the first predetermined time period when the lesion candidate region L is detected in the detecting section 34.

The memory 36d is configured to be capable of temporarily storing the still image G4.

When determining that the lesion candidate region L is continuously detected, the detection-result output section 36 causes the memory 36d to temporarily store the still image G4.

As shown in FIG. 7, after the elapse of the first predetermined time period, the detection-result output section 36 adds a marker image G2a to the still image G4 temporarily stored in the memory 36d and displays the still image G4. When the second predetermined time period further elapses after the elapse of the first predetermined time period, the detection-result output section 36 hides the still image G4.

According to the modification of the first embodiment explained above, it is possible to more surely show the position of the lesion candidate region L to the surgeon. It is possible to prevent a decrease in attention to the observation image G1 and present the region of interest to the surgeon without hindering an effort to improve the lesioned part finding ability.

Second Embodiment

In the first embodiment and the modification of the first embodiment explained above, the emphasis processing is started when the lesion candidate region L is continuously detected for the first predetermined time period. However, the emphasis processing section 36a may start the emphasis processing when the lesion candidate region L is continuously detected for the first predetermined time period and an operation section is in an ON state.

Figure 8:
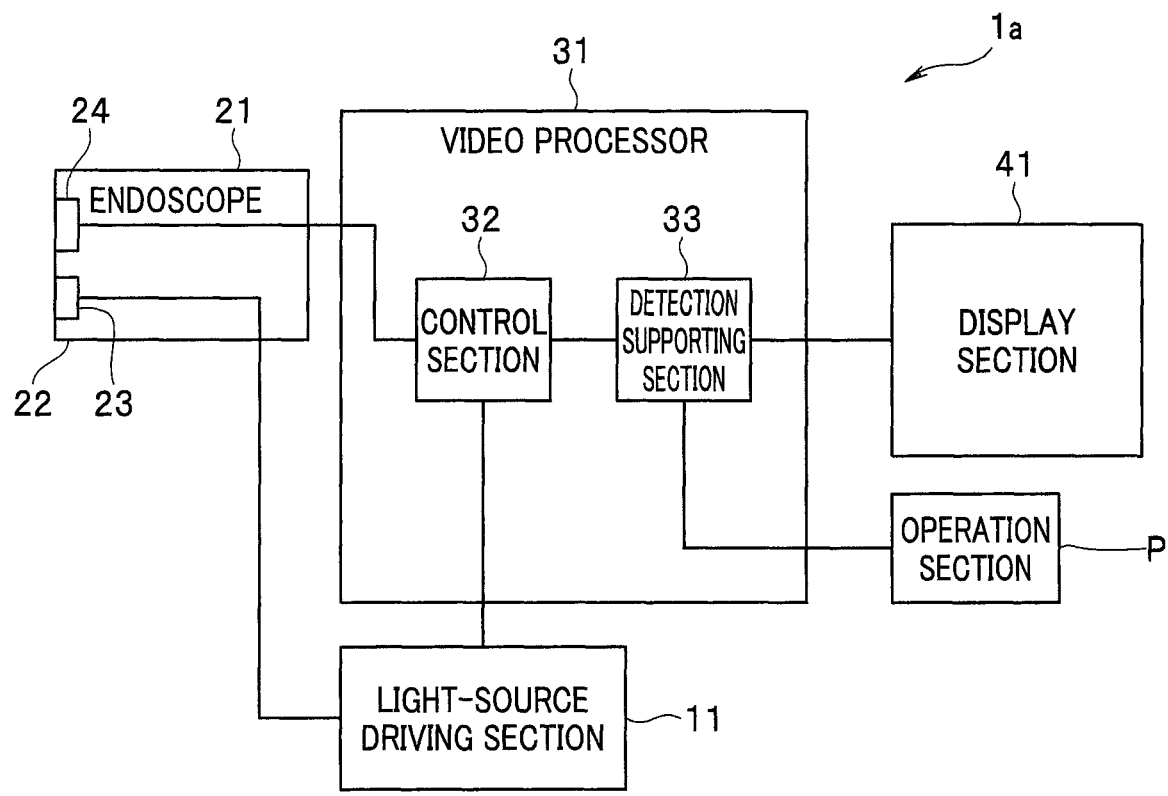
FIG. 8 is a block diagram showing a schematic configuration of an endoscope system according to a second embodiment of the present invention.
Figure 9:
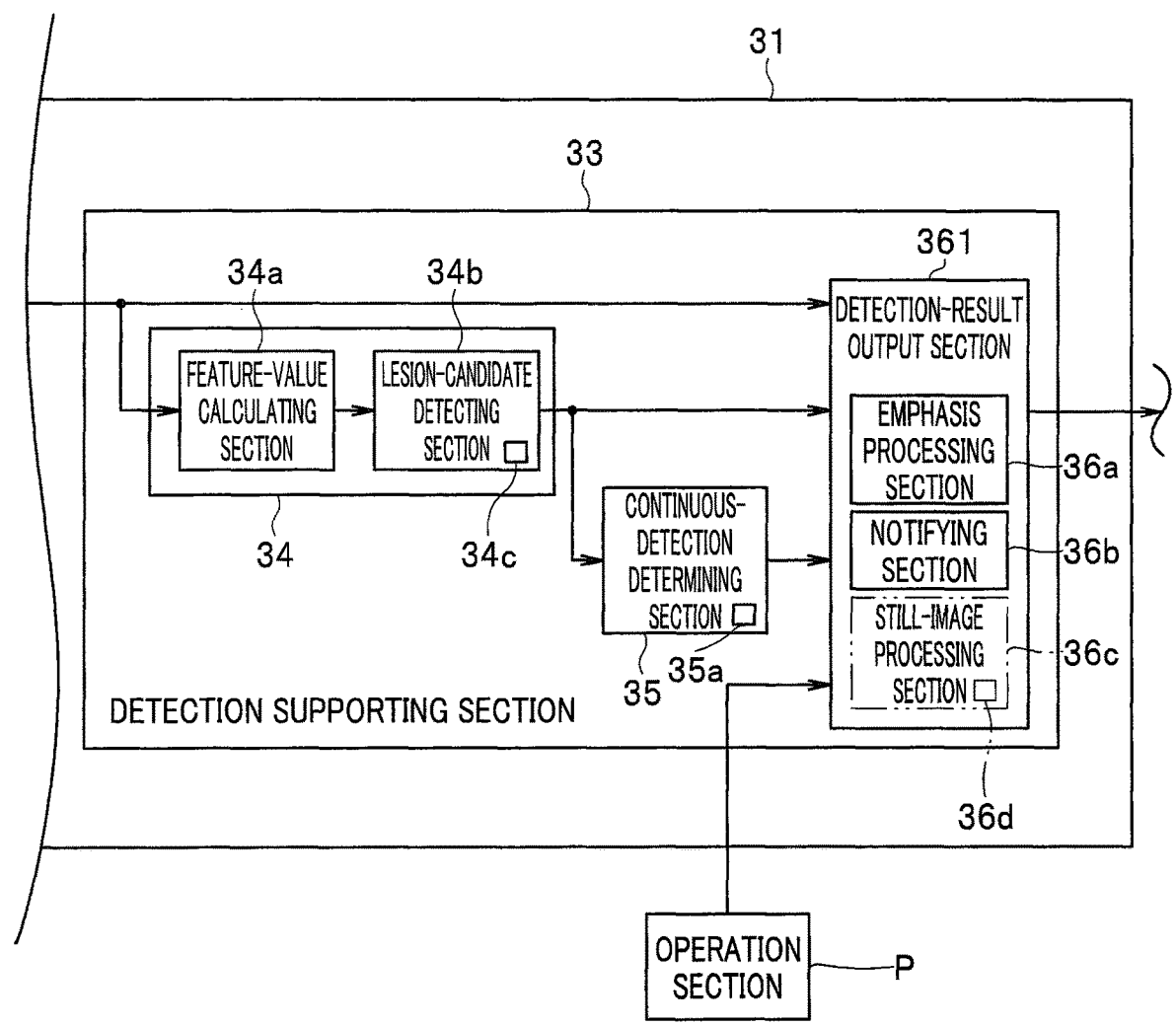
FIG. 9 is a block diagram showing the configuration of a detection supporting section of the endoscope system according to the second embodiment of the present invention.

FIG. 8 is a block diagram showing a schematic configuration of an endoscope system 1a according to a second embodiment of the present invention. FIG. 9 is a block diagram showing the configuration of the detection supporting section 33 of the endoscope system 1a according to the second embodiment of the present invention. In the explanation of the second embodiment, the same components as the components in the first embodiment and the modification of the first embodiment are denoted by the same reference numerals and signs and explanation of the components is omitted.

The endoscope apparatus 1a in the second embodiment includes an operation section P and a detection-result output section 361.

The operation section P is configured by a switch capable of switching an ON state and an OFF state according to an operation instruction of a surgeon. The operation section P is connected to the detection-result output section 361.

The detection-result output section 361 is configured to be capable of detecting the ON/OFF state of the operation section P. The emphasis processing section 36a starts the emphasis processing when the lesion candidate region L is continuously detected for the first predetermined time period and it is detected that the operation section P is in the ON state.

Subsequently, detection result output processing in the detection-result output section 361 is explained.

Figure 10:
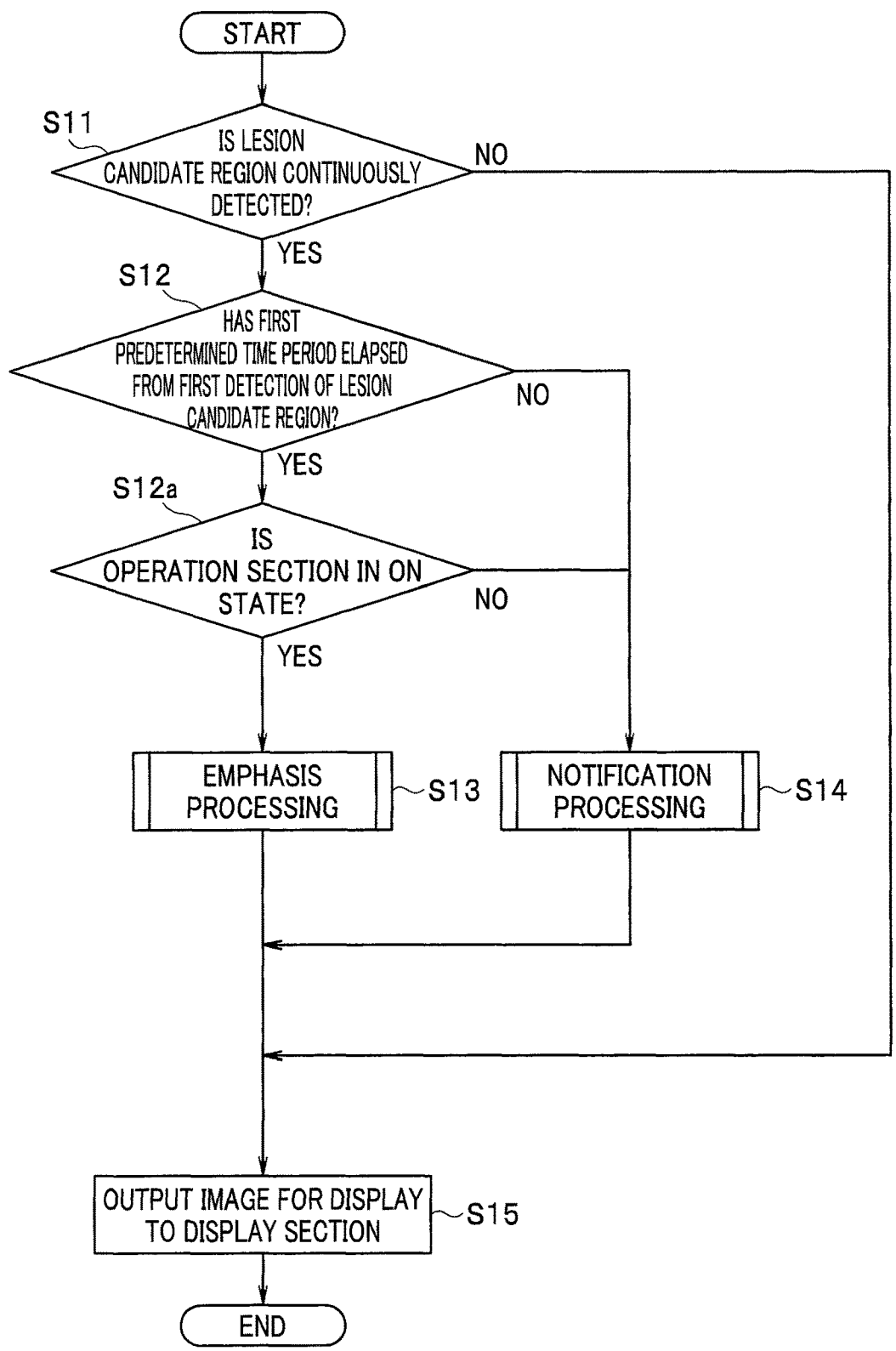
FIG. 10 is a flowchart for explaining a flow of the detection result output processing of the endoscope system according to the second embodiment of the present invention.

FIG. 10 is a flowchart for explaining a flow of the detection result output processing of the endoscope system 1a according to the second embodiment of the present invention.

The detection-result output section 361 determines whether the lesion candidate region L is continuously detected (S11). In S11, the detection-result output section 361 refers to a determination result inputted from the continuous-detection determining section 35. When the detection-result output section 361 determines that the lesion candidate region L is continuously detected (S11: Yes), the processing proceeds to S12. On the other hand, when the detection-result output section 361 determines that the lesion candidate region L is not continuously detected (S11: No), the processing proceeds to S15.

The detection-result output section 361 determines whether the first predetermined time period elapses from first detection of the lesion candidate region L (S12). In S12, when the detection-result output section 361 determines that the first predetermined time period elapses from the first detection of the lesion candidate region L (S12: YES), the processing proceeds to S13. When the detection-result output section 361 determines that the first predetermined time period does not elapse from the first detection of the lesion candidate region L (S12: NO), the processing proceeds to S14.

In S13, the detection-result output section 361 applies the emphasis processing to the observation image G1. After the processing in S13, the processing proceeds to S15.

In S14, the detection-result output section 361 applies the notification processing to the image for display G. After the processing in S14, the processing proceeds to S15.

The detection-result output section 361 outputs the image for display G to the display section 41 (S15).

The processing in S11 to S15 configures the detection result output processing.

Figure 11:
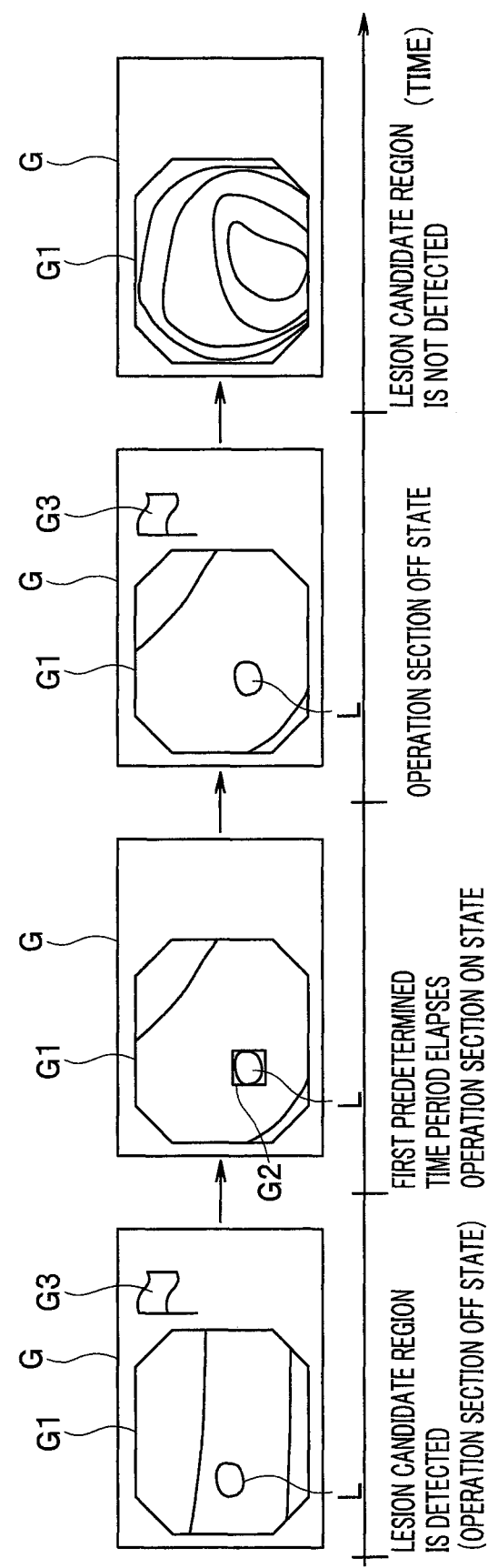
FIG. 11 is an explanatory diagram for explaining an example of screen transition in the detection result output processing of the endoscope system according to the second embodiment of the present invention.

FIG. 11 is an explanatory diagram for explaining an example of screen transition in the detection result output processing of the endoscope system 1a according to the second embodiment of the present invention.

The detection result output processing in S11 to S15 is repeated, whereby the image for display G transitions as shown in FIG. 11.

When the lesion candidate region L is continuously detected, the notification processing is started by the notifying section 36b. In the image for display G, the notification image G3 is displayed. Subsequently, when the lesion candidate region L is continuously detected for the first predetermined time period and it is detected that the operation section P is in the ON state, the emphasis processing is started by the emphasis processing section 36a. In the observation image G1 of the image for display G, the marker image G2 is displayed. Subsequently, when the operation section P is switched to the OFF state according to an operation instruction of the surgeon and the detection-result output section 361 detects that the operation section P is in the OFF state, the emphasis processing is ended. On the other hand, the notification processing is started by the notifying section 36b. In the image for display G, the marker image G2 is hidden and the notification image G3 is displayed. Subsequently, when the lesion candidate region L is not detected, the notification processing is ended. In the image for display G, the notification image G3 is hidden.

Consequently, in the endoscope system 1a, when the operation section P is switched to the OFF state according to an operation instruction of the surgeon, the marker image G2 is hidden. In the endoscope system 1a, when the operation section P is in the ON state and the lesion candidate region L is continuously detected for the first predetermined time period, the marker image G2 is displayed. In the endoscope system 1a, when the first predetermined time period does not elapse from the first detection of the lesion candidate region L when the operation section P is switched from the OFF state to the ON state by the surgeon, the marker image G2 is displayed after the elapse of the first predetermined time period from the first detection of the lesion candidate region L.

According to the second embodiment explained above, there is a time period in which the surgeon visually finds a lesioned part by himself or herself from a time when the lesion candidate region L is detected until the marker image G2 is displayed. It is possible to hide the marker image G2 according to an operation instruction of the surgeon. Therefore, it is possible to prevent a decrease in attention to the observation image G1 and present a region of interest to the surgeon without hindering an effort to improve a lesioned part finding ability. Since the operation section P has to be switched from the OFF state to the ON state only when necessary, the operation section P is switched to the OFF state when the marker image G2 is unnecessary. Therefore, the surgeon does not feel annoyed by display of the marker image G2 in the lesion candidate region L already noticed.

Third Embodiment

In the first embodiment, the modification of the first embodiment, and the second embodiment explained above, one monitor configures the display section 41. However, the display section 41 may include two monitors.

Figure 12:
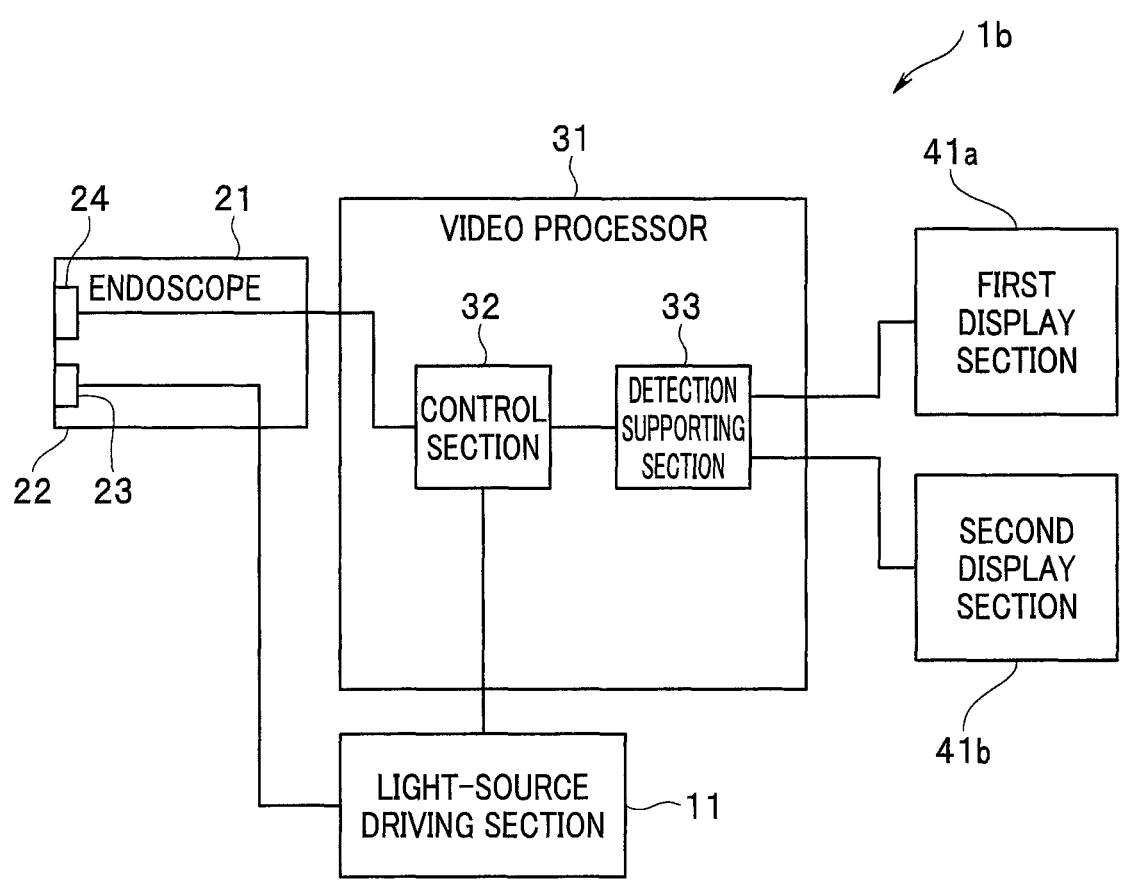
FIG. 12 is a block diagram showing a schematic configuration of an endoscope system according to a third embodiment of the present invention.
Figure 13:
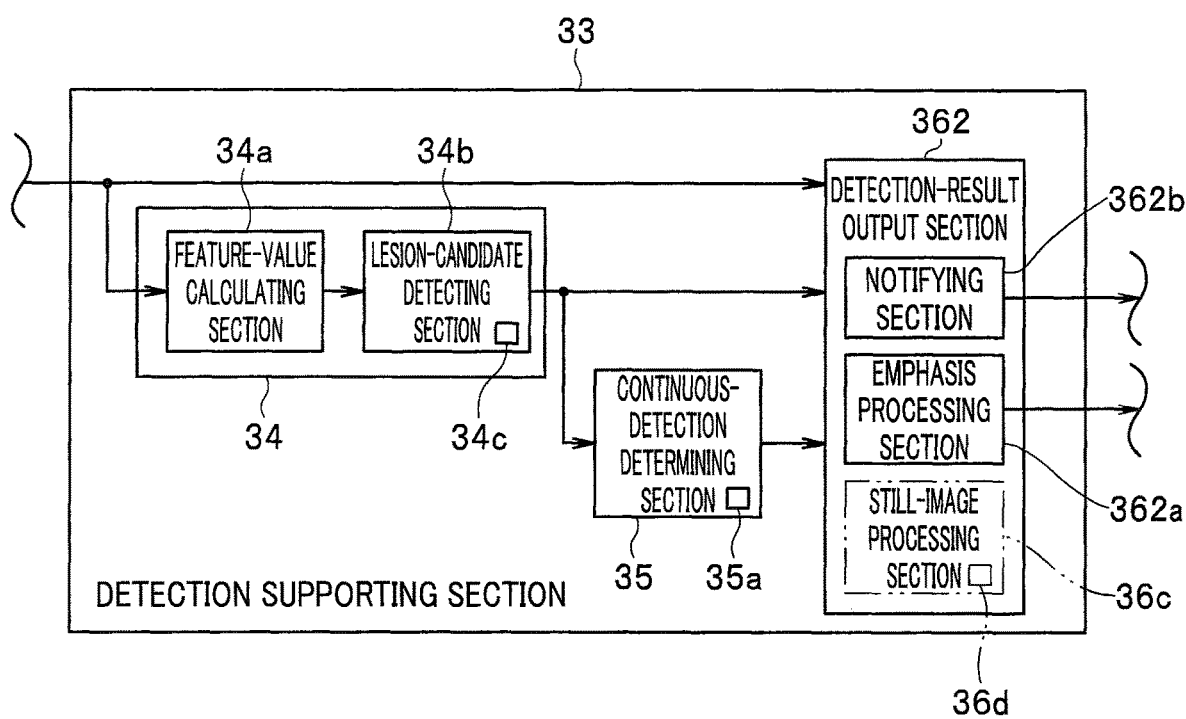
FIG. 13 is a block diagram showing the configuration of a detection supporting section of the endoscope system according to the third embodiment of the present invention.
Figure 14:
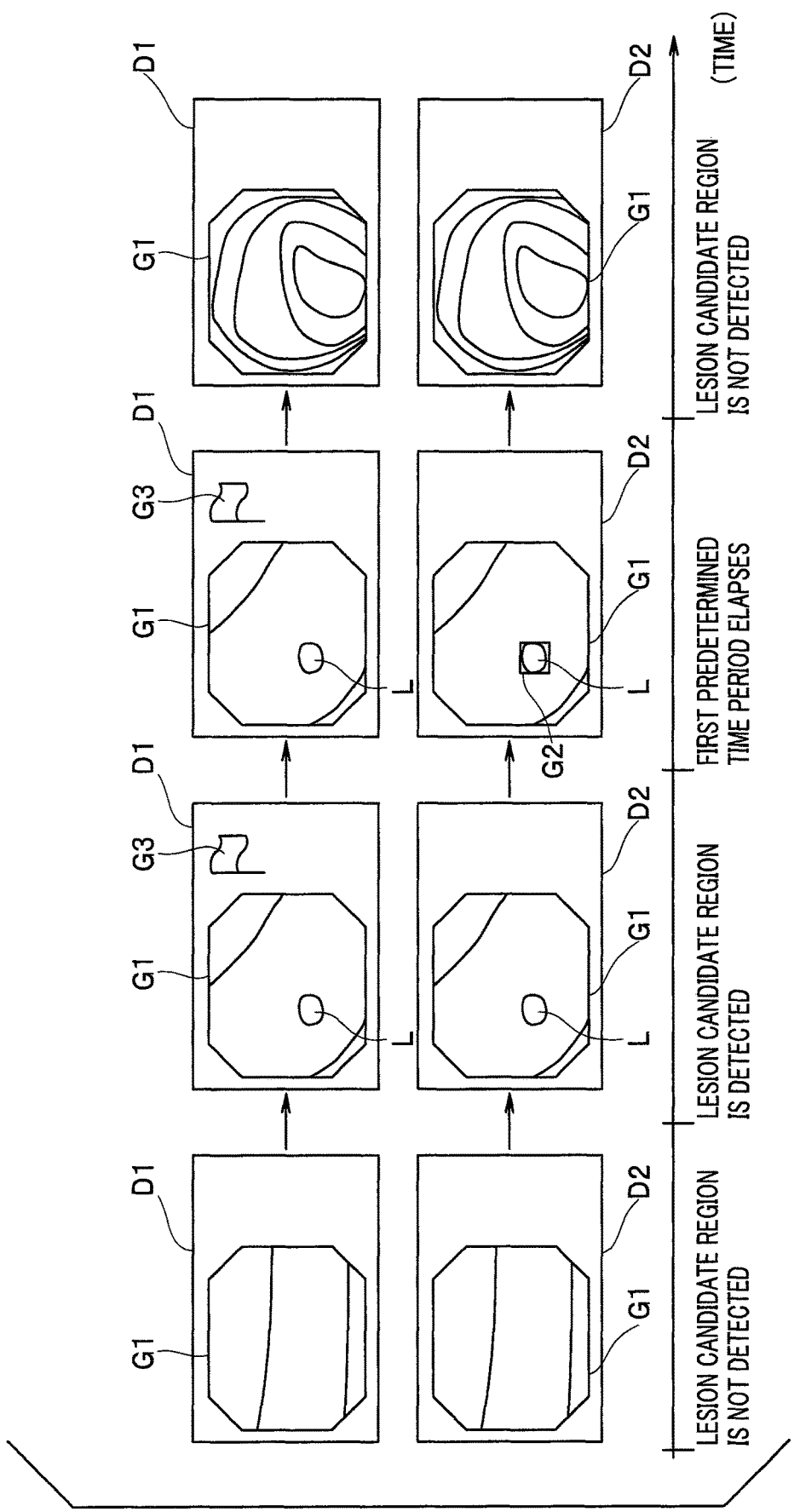
FIG. 14 is an explanatory diagram for explaining an example of screen transition in the detection result output processing of the endoscope system according to the third embodiment of the present invention.

FIG. 12 is a block diagram showing a schematic configuration of an endoscope system 1b according to a third embodiment of the present invention. FIG. 13 is a block diagram showing the configuration of the detection supporting section 33 of the endoscope system 1b according to the third embodiment of the present invention. FIG. 14 is an explanatory diagram for explaining an example of screen transition in the detection result output processing of the endoscope system 1b according to the third embodiment of the present invention. In the explanation of the third embodiment, the same components as the components in the first embodiment, the modification of the first embodiment, and the second embodiment are denoted by the same reference numerals and signs and explanation of the components is omitted.

The endoscope system 1b includes, as shown in FIG. 12, a first display section 41a and a second display section 41b. A detection-result output section 362 of the endoscope system 1b includes, as shown in FIG. 13, a notifying section 362b and an emphasis processing section 362a.

Each of the first display section 41a and the second display section 41b is configured by a monitor capable of displaying an image.

The first display section 41a is connected to the notifying section 362b and is capable of displaying a first image for display D1 outputted from the notifying section 362b.

The second display section 41b is connected to the emphasis processing section 362a and is capable of displaying a second image for display D2 outputted from the emphasis processing section 362a.

When the lesion candidate region L is detected in the observation image G1 by the detecting section 34, the notifying section 362b performs notification processing for notifying a surgeon that the lesion candidate region L is detected, generates the first image for display D1, and outputs the first image for display D1 to the first display section 41a.

When the lesion candidate region L is continuously detected in the lesion-candidate detecting section 34b, the emphasis processing section 362a applies emphasis processing of a position corresponding to the lesion candidate region L to the observation image G1 of the subject inputted after the elapse of the first predetermined time period from a time when the lesion candidate region L is detected, generates the second image for display D2, and outputs the second image for display D2 to the second display section 41b.

FIG. 14 is an explanatory diagram for explaining an example of screen transition in the detection result output processing of the endoscope system 1b according to the third embodiment of the present invention.

When the lesion candidate region L is continuously detected, the notification processing is started by the notifying section 362b. In the first image for display D1, the notification image G3 is displayed. Subsequently, when the lesion candidate region L is continuously detected for the first predetermined time period, the emphasis processing is started by the emphasis processing section 362a. In the second image for display D2, the marker image G2 is displayed. Subsequently, when the lesion candidate region L is not detected, the emphasis processing and the notification processing are ended. The marker image G2 and the notification image G3 are hidden.

Consequently, the surgeon is capable of observing the first image for display D1 displayed on the first display section 41a, which is a main screen, and observing, according to necessity, the second image for display D2 displayed on the second display section 41b, which is a sub-screen. For example, the surgeon is capable of performing observation of the subject with the first image for display D1 and, when the notification image G3 is displayed in the first image for display D1, more carefully observing the first image for display D1, and visually finding a lesioned part by himself or herself. Further, when a lesioned part cannot be found on the first image for display D1, the surgeon is capable of shifting the eyes to the second image for display D2 according to necessity and more carefully confirming the lesion candidate region L based on a display position of the marker image G2 displayed after the elapse of the first predetermined time period from the detection of the lesion candidate region L.

According to the third embodiment explained above, there is a time period in which the surgeon visually finds a lesioned part by himself or herself from the time when the lesion candidate region L is detected until the marker image G2 is displayed. The marker image G2 is displayed in the second image for display D2. Therefore, it is possible to prevent a decrease in attention to the observation image G1 in the first image for display D1 and present a region of interest to the surgeon without hindering an effort to improve a lesioned part finding ability. Since the surgeon has to view, only when necessary, the second image for display D2 in which the marker image G2 is displayed, the surgeon views the first image for display D1 without the marker image G2 when the marker image G2 is unnecessary. Therefore, the surgeon does not feel annoyed by display of the marker image G2 in the lesion candidate region L already noticed.

Note that, in the embodiment, for explanation, one lesion candidate region L is displayed on the observation screen. However, a plurality of lesion candidate regions L are displayed on the observation screen in some cases. In such a case, the emphasis processing is applied to the respective lesion candidate regions L. The emphasis processing of the respective lesion candidate regions L is applied to the observation image G1 inputted after the elapse of the first predetermined time period from detection of the respective lesion candidate regions L.

Note that, in the embodiment, the first predetermined time period and the second predetermined time period are set in advance and fixed. However, the setting of the first predetermined time period and the second predetermined time period may be changeable by the operation section P (FIG. 8 and FIG. 9) or a not-shown another operation section. With this configuration, the surgeon is capable of changing the first predetermined time period and the second predetermined time period to desired time periods.

Note that, in the embodiment, the control section 32 applies image adjustment such as gain adjustment, white balance adjustment, gamma correction, contour emphasis correction, and enlargement and reduction adjustment to an image pickup signal inputted from the endoscope 21 and inputs the observation image G1 after the image adjustment to the detection supporting section 33. However, a part or the entire image adjustment may be applied to an image signal outputted from the detection supporting section 33 rather than before the image signal is inputted to the detection supporting section 33.

Note that, in this embodiment, the detection supporting section 33 is disposed on the inside of the video processor 31. For example, the detection supporting section 33 may be disposed on an outside of the video processor 31, for example, between the video processor 31 and the display section 41.

Furthermore, in the embodiment, the emphasis processing section 36a adds the marker image G2 to the lesion candidate region L. However, the marker image G2 may be classified by color and displayed according to likelihood of the detected lesion candidate region L. In this case, the lesion-candidate detecting section 34b outputs lesion candidate information including likelihood information of the lesion candidate region L to the emphasis processing section 36a. The emphasis processing section 36a performs the emphasis processing according to the color classification based on the likelihood information of the lesion candidate region L. With this configuration, when the surgeon observes the lesion candidate region L, the surgeon is capable of estimating a level of possibility of false positive (error detection) according to a color of the marker image G2.

In the first embodiment, the modification of the first embodiment, and the second embodiment, the notification processing is performed until the lesion candidate region L is not detected by the detecting section 34 after the elapse of the second predetermined time period. However, the notification processing may be performed until a start of the emphasis processing after the lesion candidate region L is detected. With this configuration, until the marker image G2 is displayed after the lesion candidate region L is detected, the surgeon is capable of recognizing that the lesion candidate region L is detected somewhere on the observation image G1. A lesioned part is easily found. The notification processing may be performed in parallel to the emphasis processing. The notification processing may be continuously performed until the lesion candidate region L is not detected by the detecting section 34 after the lesion candidate region L is detected.

Note that, in the first embodiment, the modification of the first embodiment, and the second embodiment, the notification processing is performed until the lesion candidate region L is not detected by the detecting section 34 after the elapse of the second predetermined time period. However, the notifying section 36b may start the notification processing after the emphasis processing is started. With this configuration, the notification processing is performed in addition to the display of the marker image G2. The surgeon is capable of more surely recognizing that the lesion candidate region L is detected.

Figure 15:
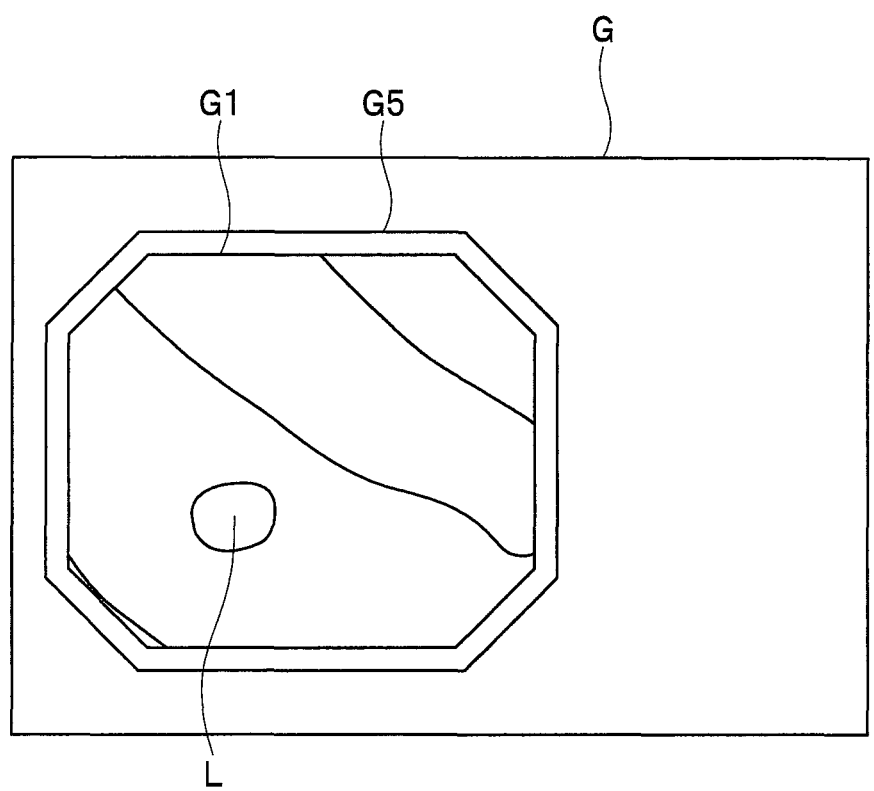
FIG. 15 is an explanatory diagram for explaining an example of a screen configuration of an image for display of the endoscope system according to the first embodiment of the present invention.

Note that, for example, in the embodiment, the notifying section 36b displays the notification image G3 in a region other than the observation image G1. However, as shown in FIG. 15, the notifying section 36b may display an image G5 surrounding the observation image G1. With this configuration, with the display of the image G5 surrounding the observation image G1, irrespective of to which portion of the observation image G1 the surgeon is paying attention, the surgeon easily notices that the lesion candidate region L is detected.

Note that, in the embodiment, the notifying section 36b displays the notification image G3 to thereby notify the surgeon that the lesion candidate region L is detected. However, the notifying section 36b may emit a sound from a not-shown speaker to notify the surgeon that the lesion candidate region L is detected.

Note that, in the embodiment, the detection supporting section 33 is configured by a circuit. However, the respective functions of the detection supporting section 33 may be configured by processing programs for realizing the functions according to processing of a CPU.

The present invention is not limited to the embodiments explained above. Various changes, alterations, and the like are possible in a range in which the gist of the present invention is not changed.

According to the present invention, it is possible to provide an endoscope apparatus that prevents a decrease in attention to an observation image and presents a region of interest to the surgeon without hindering an effort to improve a lesioned part finding ability.

What is claimed is:

1. An endoscope apparatus comprising:
a processor configured to:
sequentially receive observation images of a subject and detect a characteristic region in the observation images based on a predetermined feature value;
determine a time when the characteristic region is detected in the sequentially received observation images;
determine an elapsed time period from the time when the characteristic region is detected in the sequentially received observation images;
selectively apply a predetermined emphasis processing to one or more images of the observation images to emphasize a position of the characteristic region in the one or more images of the observation images,
wherein in response to determining that the elapsed time period is less than a first predetermined time period, the processor is configured to not apply the predetermined emphasis processing to one or more images of the observation images received during the elapsed time period, and
wherein in response to determining that the elapsed time period is equal to the first predetermined time period, the processor is configured to apply the predetermined emphasis processing to one or more images of the observation images received after the first predetermined time period; and
control a monitor to display the observation images having the predetermined emphasis processing selectively applied to one or more of the observation images.

2. The endoscope apparatus according to claim 1, wherein the processor is configured to, in response to determining that the elapsed time period is equal to the first predetermined time period, apply the predetermined emphasis processing to the one or more images of the observation images received for a second predetermined time period and end application of the predetermined emphasis processing after the elapsed time period is equal to the second predetermined time period.

3. The endoscope apparatus according to claim 2, wherein the processor is configured to, in response to determining that the elapsed time period is equal to the second predetermined time period, selectively apply a notification processing, different from the predetermined emphasis processing, to one or more images of the observation images received after the second predetermined time period to notify of presence of the characteristic region in the one or more images of the observation images.

4. The endoscope apparatus according to claim 3, wherein the processor is configured to end application of the notification processing after the characteristic region is not detected.

5. The endoscope apparatus according to claim 3, wherein the processor is configured to end application of the notification processing after the predetermined emphasis processing is applied again after the characteristic region is detected again.

6. The endoscope apparatus according to claim 3, wherein the processor is configured to end application of the notification processing after the characteristic region is not detected after the characteristic region is detected.

7. The endoscope apparatus according to claim 3, wherein the notification processing is processing for displaying an image surrounding an image of the observation images displayed on the monitor.

8. The endoscope apparatus according to claim 3, wherein the processor is configured to control another monitor display a result of the notification processing.

9. The endoscope apparatus according to claim 3, wherein the processor is configured to control a speaker to emit a sound as the notification processing applied to the one or more images of the observation images received after the second predetermined time period.

10. The endoscope apparatus according to claim 2, wherein the first predetermined time period and the second predetermined time period are specified by a number of frames.

11. The endoscope apparatus according to claim 2, wherein the processor is configured to determine whether a first characteristic region on a first observation image of the observation images and a second characteristic region on a second observation image of the observation images received before the first observation image are both the characteristic region.

12. The endoscope apparatus according to claim 11, wherein, when the characteristic region is continuously or intermittently detected, the processor is configured to determine that the characteristic region is continuously detected.

13. The endoscope apparatus according to claim 11, wherein, when the characteristic region determined as being continuously detected is continuously detected for the first predetermined time period, the processor is configured to start the predetermined emphasis processing.

14. The endoscope apparatus according to claim 11, wherein, when the characteristic region determined as being continuously detected is continuously detected even when the second predetermined time period elapses after the elapse of the first predetermined time period, the processor is configured to end the predetermined emphasis processing.

15. The endoscope apparatus according to claim 2, comprising an operation switch configured to enable the first predetermined time period and the second predetermined time period to be set and inputted by the operation switch.

16. The endoscope apparatus according to claim 1, wherein the processor is configured to:
determine likelihood information of the characteristic region detected, as a target candidate region, being a target; and
perform the predetermined emphasis processing according to color classification based on the likelihood information.

17. The endoscope apparatus according to claim 1, wherein the processor is configured to control the monitor to display an image of the observation images as a still image after the elapse time period has reached the first predetermined time period.

18. The endoscope apparatus according to claim 1, wherein the predetermined emphasis processing is processing for performing display showing the position of the characteristic region.

19. The endoscope apparatus according to claim 1, comprising an operation switch configured to be switchable between an ON state and an OFF state,
wherein the processor is configured to, in response to determining that the elapsed time period has reached the first predetermined time period and that the operation switch is in the ON state, apply the predetermined emphasis processing to the one or more images of the observation images received after the first predetermined time period.

20. The endoscope apparatus according to claim 1, wherein the characteristic region is a lesion candidate region.

21. The endoscope apparatus according to claim 20, wherein the lesion candidate region is a polyp.

* * * * *